(12) United States Patent
Katsuyama et al.

(10) Patent No.: US 7,977,955 B2
(45) Date of Patent: Jul. 12, 2011

(54) PARTICULATE MATTER SENSOR

(75) Inventors: Kyosuke Katsuyama, Nagoya (JP); Kenshin Kitoh, Nagoya (JP); Takeshi Sakuma, Nagoya (JP); Yukio Miyairi, Nagoya (JP); Junichi Suzuki, Kuwana (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/544,538

(22) Filed: Aug. 20, 2009

(65) Prior Publication Data
US 2009/0309571 A1   Dec. 17, 2009

Related U.S. Application Data

(63) Continuation of application No. PCT/JP2008/055928, filed on Mar. 27, 2008.

(30) Foreign Application Priority Data

Mar. 27, 2007   (JP) .................................. 2007-082058

(51) Int. Cl.
*G01R 27/08* (2006.01)
*G01N 7/00* (2006.01)
(52) U.S. Cl. ........................ 324/693; 73/23.31; 73/23.32
(58) Field of Classification Search .................. 324/71.1, 324/693; 73/23.31
See application file for complete search history.

(56) References Cited

U.S. PATENT DOCUMENTS

| 4,656,832 A * | 4/1987 | Yukihisa et al. ................ 60/303 |
| 2003/0102854 A1 | 6/2003 | Gascoyne et al. |
| 2008/0048681 A1 | 2/2008 | Birkhofer et al. |

FOREIGN PATENT DOCUMENTS

| JP | S58-020919 | 2/1983 |
| JP | S59-60018 | 4/1984 |
| JP | S59-196453 | 11/1984 |
| JP | H04-203413 | 7/1992 |
| JP | 2005-512042 | 4/2005 |
| WO | 93/08382 | 4/1993 |
| WO | WO9308382 | * 4/1993 |
| WO | 03/048728 | 6/2003 |
| WO | 2005/093233 | 10/2005 |

* cited by examiner

*Primary Examiner* — Melissa J Koval
(74) *Attorney, Agent, or Firm* — Burr & Brown (57) ABSTRACT

A particulate matter sensor which may be used as an onboard particulate matter diagnostic sensor includes an insulating base that has at least a pair of opposing plane surfaces, an electrode nucleus that is formed on one of the pair of opposing plane surfaces of the base, and forms an electrode when a conductive substance adheres to the plane surface, and an electrode that is disposed parallel to the electrode nucleus and is provided on the other of the pair of opposing plane surfaces, or provided on a side surface of the base that is adjacent to the pair of opposing plane surfaces, or provided inside the base.

11 Claims, 4 Drawing Sheets

FIG.14 ic matter sensor" >
PARTICULATE MATTER SENSOR

FIELD OF THE INVENTION

The present invention relates to a particulate matter sensor. More particularly, the present invention relates to a particulate matter sensor that may be utilized to measure the amount of particulate matter (PM) discharged from an internal combustion engine, or may be utilized for onboard diagnosis (OBD) that deals with particulate matter (PM) regulations.

BACKGROUND OF THE INVENTION

Regulations concerning exhaust amount of toxic substances contained in automotive exhaust gas have been increasingly tightened. In the United States, it is said that an onboard particulate matter diagnostic system will be essential in 2010, for example.

It has been reported that a gasoline-powered vehicle that employs a direct injection system discharges particulate matter (PM) in an amount larger than that of a diesel-powered vehicle provided with a diesel particulate filter (DPF).

Patent Document 1 focuses on the fact that particulate matter contained in exhaust gas consists of conductive particles, and discloses a particulate matter detection element and a particulate matter detection filter that utilize a phenomenon in which the electrical resistance of an electrical insulating member decreases when conductive particulate matter adheres to the electrical insulating member.

Patent Document 2 discloses technology that receives light that has been emitted from a light source and passed through an exhaust gas flow using a light-receiving section, detects the opacity of the exhaust gas that has a constant correlation function with the particulate matter concentration, and converts the detected opacity into the particulate matter concentration using a control means.

Patent Document 1: JP-A-59-060018
Patent Document 2: JP-A-04-203413

SUMMARY OF THE INVENTION

The invention disclosed in Patent Document 1 has a problem in that the measurement cannot be performed if an appropriate amount of particulate matter is not deposited between the electrodes. Moreover, since the contact state of the particles with each other changes depending on the deposition state (i.e., bulk density) of the particulate matter, the electrical resistance may vary even if the same amount of particulate matter is deposited, so that the measurement accuracy may be adversely affected.

According to the invention disclosed in Patent Document 2 in which the opacity to light passing through the exhaust gas pipe is measured, the entire exhaust gas flow can be measured. However, as the window of the light-emitting/light-receiving section becomes dirty, the measurement accuracy gradually deteriorates.

The present invention was conceived in view of the above problems. An object of the present invention is to provide a high-sensitivity particulate matter sensor.

The inventors of the present invention conducted extensive studies in order to achieve the above object. As a result, the inventors found that the above object can be achieved by a specific particulate matter sensor and a specific particulate matter amount measuring method given below. This finding has led to completion of the present invention.

Specifically, the present invention provides the following particulate matter sensor and particulate matter amount measuring method.

According to a first aspect of the present invention, the particulate matter sensor comprises an insulating base that has at least a pair of opposing plane surfaces, an electrode nucleus that is formed on one of the pair of opposing plane surfaces of the base, and forms an electrode when a conductive substance adheres to the plane surface, and an electrode that is disposed parallel to the electrode nucleus and is provided on the other of the pair of opposing plane surfaces, or provided on a side surface of the base that is adjacent to the pair of opposing plane surfaces, or provided inside the base.

According to a second aspect of the present invention, the particulate matter sensor according to the first aspect is provided, wherein the base has a plurality of through-holes that are formed through the pair of opposing plane surfaces.

According to a third aspect of the present invention, the particulate matter sensor according to the first or second aspect is provided, wherein the plane surface on which the electrode nucleus is formed has a centerline average roughness of 0.2 to 200 μm.

According to a fourth aspect of the present invention, the particulate matter sensor according to any one of the first through third aspects is provided, wherein the electrode nucleus has an area corresponding to 50% or less of the area of the electrode parallel to the electrode nucleus.

According to a fifth aspect of the present invention, the particulate matter sensor according to any one of the first through fourth aspects is provided, further comprising an isolated electrode nucleus that is electrically isolated from the electrode nucleus.

According to a sixth aspect of the present invention, the particulate matter sensor according to any one of the first through fifth aspects is provided, further comprising a heater that is provided inside the base, or provided on the side surface of the base that is adjacent to the pair of opposing plane surfaces, or provided on the plane surface on which the electrode nucleus is not formed.

According to a seventh aspect of the present invention, the particulate matter sensor according to any one of the first through sixth aspects is provided, wherein the electrode nucleus and the electrode are electrically connected When a conductive substance adheres to the base.

According to an eighth aspect of the present invention, the particulate matter measuring method comprises disposing an electrode nucleus on at least one of a pair of opposing plane surfaces of an insulating base, and disposing an electrode that is parallel to the electrode nucleus, the electrode nucleus forming an electrode when a conductive substance adheres to the plane surface, and the electrode being provided on the other of the pair of opposing plane surfaces, or provided on a side surface of the base that is adjacent to the pair of opposing plane surfaces, or provided inside the base; disposing the base in a gas passage so that the plane surface on which the electrode nucleus is formed is positioned on an upstream side in the gas passage; measuring the impedance between the electrode nucleus and the electrode while causing an alternating current to flow between the electrode nucleus and the electrode; and determining the amount of conductive particulate matter that adheres to the base based on the impedance that has been measured.

The particulate matter sensor according to the present invention can measure the amount of particulate matter contained in exhaust gas with high sensitivity. Since the particulate matter contained in exhaust gas is conductive and the impedance is inversely proportional to the electrode area, the amount of particulate matter that adheres to the base can be determined with high sensitivity by measuring the impedance utilizing the particulate matter that adheres to the base as an electrode ($Z=d/\in Sw$ and $w=2\pi f$; $Z$: impedance, d: electrode-to-electrode distance, $\in$: dielectric constant, S: electrode area, f: frequency of impedance measurement signal).

EXPLANATION OF SYMBOLS

1: particulate matter sensor, 2: base, 3: electrode nucleus, 4: electrode, 5: circulation hole, 6: isolated electrode nucleus, 7: plug, 8: heater, 10: gas flow

DETAILED DESCRIPTION OF THE INVENTION

Best mode of the present invention are described below. Note that the present invention is not limited to the following embodiments. Various modifications and improvements may be made of the following embodiments without departing from the scope of the present invention based on the knowledge of a person skilled in the art.

Figure 1:
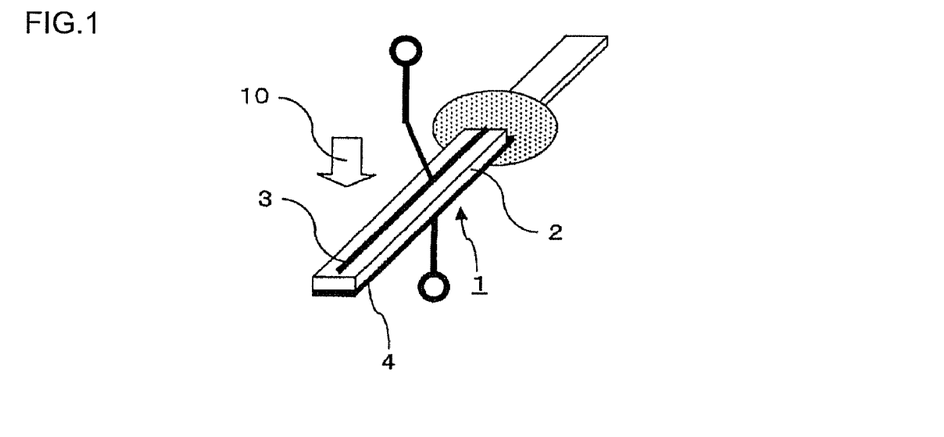
FIG. 1 is a schematic perspective view showing a particulate matter sensor according to one embodiment of the present invention.

FIG. 1 is a schematic perspective view showing a particulate matter sensor according to one embodiment of the present invention. A particulate matter sensor 1 includes a base 2, an electrode nucleus 3 that is formed on one plane surface of the base 2, and an electrode 4 that is formed on the plane surface of the base 2 opposite to the plane surface on which the electrode nucleus 3 is formed. A gas flow 10 occurs from the plane surface on which the electrode nucleus 3 is formed to the plane surface on which the electrode 4 is formed. In this case, conductive particulate matter contained in the gas flow adheres to the plane surface on which the electrode nucleus 3 is formed, and is electrically connected to the electrode nucleus 3 to function as an electrode.

Figure 2:
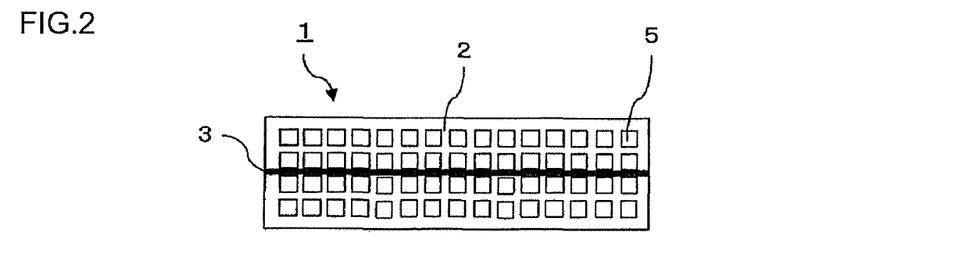
FIG. 2 is a schematic plan view showing a particulate matter sensor according to a second embodiment of the present invention.
Figure 3:
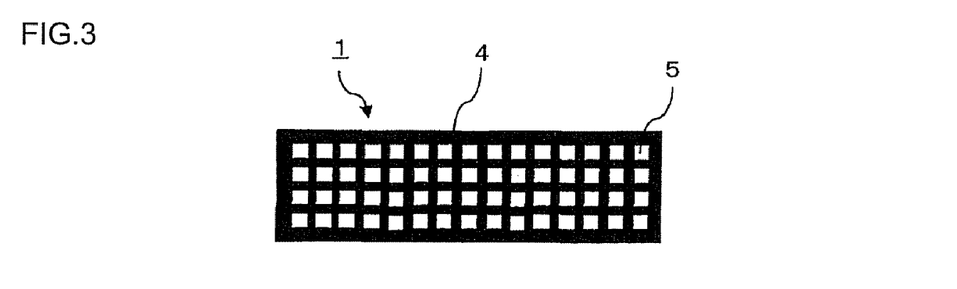
FIG. 3 is a bottom view showing the particulate matter sensor shown in FIG. 2.

FIG. 2 is a schematic plan view showing a particulate matter sensor according to a second embodiment of the present invention, and FIG. 3 is a schematic bottom view showing the particulate matter sensor shown in FIG. 2. As shown in FIG. 2, the electrode nucleus 3 is formed at the center of one plane surface of the base 2 along the longitudinal direction. As shown in FIG. 3, on the other plane surface, the electrode 4 is formed over the entire plane surface. As shown in FIGS. 2 and 3, the base 2 of the particulate matter sensor 1 has through-holes 5 that are formed through the pair of plane surfaces. This prevents a situation in which the gas flows to avoid the particulate matter sensor 1, so that the particulate matter contained in the gas does not adhere to the particulate matter sensor 1.

The shape and the size of the through-holes 5 and the interval between the through-holes 5 may be appropriately selected so that the gas flows through the particulate matter sensor 1.

Figure 4:
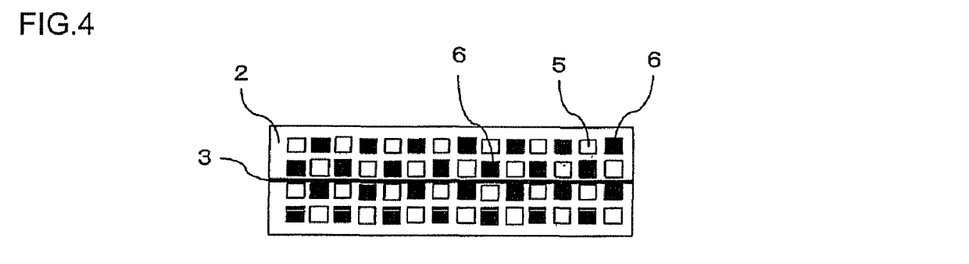
FIG. 4 is a schematic plan view showing a particulate matter sensor according to a third embodiment of the present invention.

FIG. 4 is a schematic plan view showing a particulate matter sensor according to a third embodiment of the present invention. The particulate matter sensor according to this embodiment includes isolated electrode nuclei 6 that are electrically isolated from the electrode nucleus 3. The electrode nucleus 4 and the isolated electrode nuclei 6 are electrically connected when conductive particulate matter adheres to the area that surrounds the electrode nucleus 3 and the isolated electrode nuclei 6. In this case, the area of the electrode formed by the electrode nucleus 3 and the conductive particulate matter rapidly increases when the electrode nuclei 6 are electrically connected to the electrode nucleus 4 so that the impedance between the electrodes rapidly changes. This improves detection sensitivity. In this embodiment, the through-holes are plugged in a checkered pattern, and the isolated electrode nuclei 6 are formed corresponding to the plug.

Figure 5:
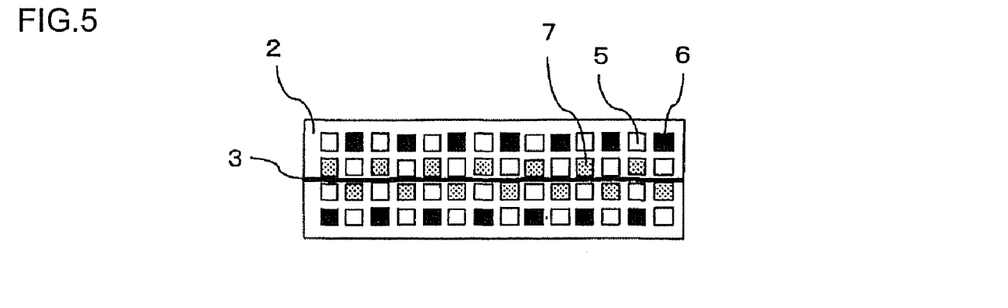
FIG. 5 is a schematic plan view showing a particulate matter sensor according to a fourth embodiment of the present invention.

The isolated electrode nuclei 6 need not necessarily be formed corresponding to all of the plug. FIG. 5 is a schematic plan view showing a particulate matter sensor according to a fourth embodiment of the present invention. In this embodiment, the isolated electrode nuclei are not formed corresponding to plug 7 positioned near the electrode nucleus. Effects similar to those of the third embodiment can also be achieved by forming the isolated electrode nuclei in this manner.

Figure 6:
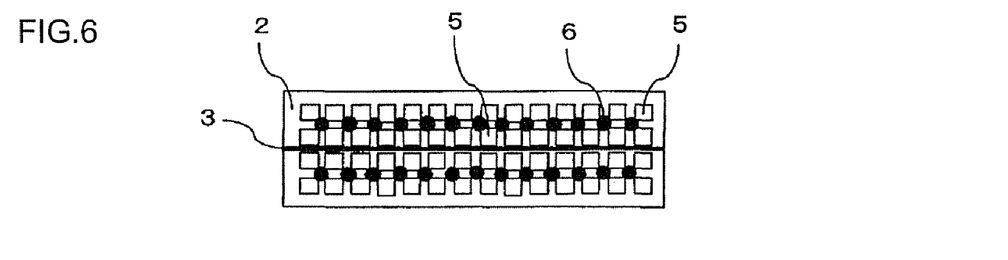
FIG. 6 is a schematic plan view showing a particulate matter sensor according to a fifth embodiment of the present invention.
Figure 7:
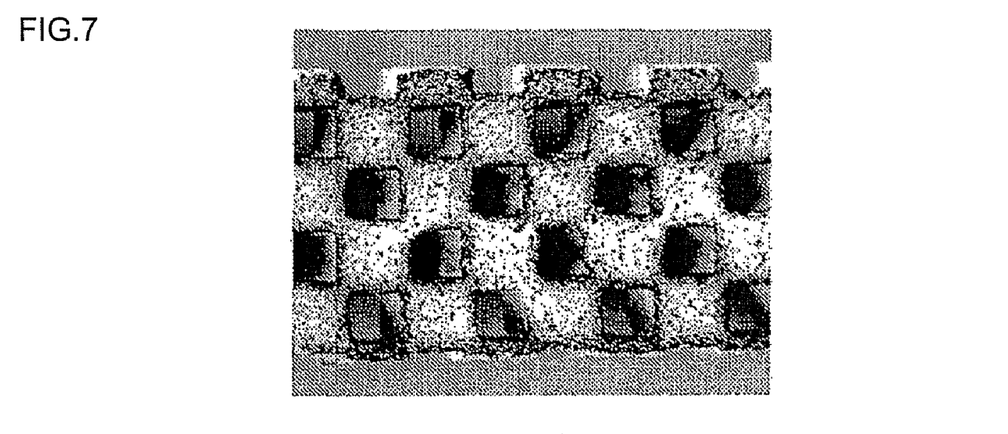
FIG. 7 is a view showing a state in which particulate matter adheres to a particulate matter sensor according to the present invention.

FIG. 6 is a schematic plan view showing a particulate matter sensor according to a fifth embodiment of the present invention. In this embodiment, the isolated electrode nuclei 6 are formed corresponding to grid points of the base 2 that are formed by forming the through-holes 5 in the base 2. FIG. 7 is a view showing a state in which particulate matter adheres to the particulate matter sensor according to the present invention. As shown in FIG. 7, the particulate matter mainly adheres to the edges of the through-holes 5. Therefore, if the isolated electrode nuclei 6 are formed corresponding to the grid points of the base 2 (see FIG. 6), the edges of the through-holes 5 to which the particulate matter adheres can be easily connected electrically with each other, so that the area of the electrode formed by the electrode nuclei and the particulate matter adhering to the base 2 can be effectively increased. As a result, sensitivity can be improved.

A heater 8 is provided in the particulate matter sensor 1 according to several embodiments of the present invention shown in FIGS. 8 to 12. In these embodiments, the heater 8 is formed using a member that generates heat when a current flows therethrough. According to these embodiments, particulate matter that adheres to the particulate matter sensor 1 can be burned out by causing the heater 8 to generate heat, so that the particulate matter sensor can be regenerated. In the present invention, the amount of particulate matter that adheres to the base is determined based on a change in conductive area on the surface of the base due to adhesion of the particulate matter. However, when a large amount of particulate matter adheres to the base, the relationship between the amount of particulate matter that adheres to the base and a change in conductive area changes. Therefore, it is effective to remove the particulate matter that adheres to the base before too large an amount of particulate matter adheres to the base in order to implement a highly accurate particulate matter measurement.

The heater 8 may also be used to make an impedance measurement condition constant. Specifically, the impedance of a substance changes corresponding to the temperature. If the temperature during the impedance measurement is made constant using the heater 8, a highly accurate particulate matter measurement can be implemented. The temperature during the impedance measurement is preferably controlled to a given temperature equal to or higher than 100° C., and more preferably 200° C., in order to avoid the effects of steam. After the given temperature has been reached, it is preferable to stop supplying power to the heater before the impedance measurement in order to prevent a leakage current.

Figure 8:
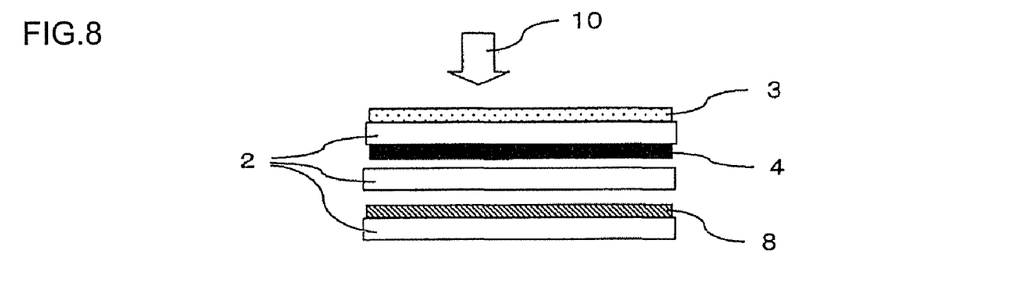
FIG. 8 is a schematic side view showing a particulate matter sensor according to a sixth embodiment of the present invention.

FIG. 8 is a schematic side view showing a particulate matter sensor according to a sixth embodiment of the present invention. The particulate matter sensor 1 according to this embodiment is formed by stacking the electrode nucleus 3, the base 2, the electrode 4, the base 2, the heater 8, and the base 2 in this order. All of them were formed in the shape of a thin sheet in advance. Through-holes may optionally be formed after stacking these elements. The electrode nucleus 3 and the electrode 4 may be formed by applying a material to the base 2. The particulate matter sensor 1 thus formed is disposed so that the gas flow 10 comes in contact with the particulate matter sensor 1 from above in FIG. 8.

Figure 9:
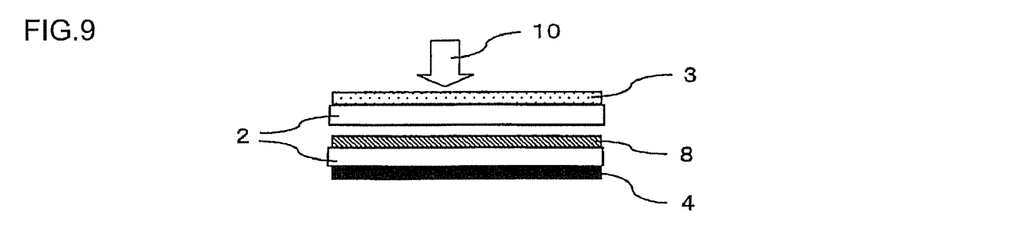
FIG. 9 is a schematic side view showing a particulate matter sensor according to a seventh embodiment of the present invention.

FIG. 9 is a schematic side view showing a particulate matter sensor according to a seventh embodiment of the present invention. The particulate matter sensor according to this embodiment is the same as the particulate matter sensor according to the sixth embodiment, except that a stacking order of the electrode 4 and the heater 8 are exchanged and the lowermost base 2 is omitted. This configuration also achieves the desired effects.

Figure 10:
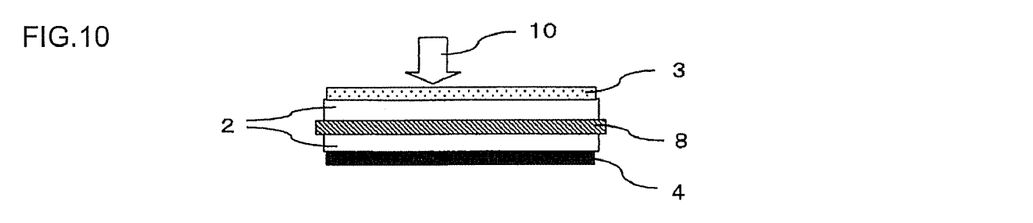
FIG. 10 is a schematic side view showing a particulate matter sensor according to an eighth embodiment of the present invention.

FIG. 10 is a schematic side view showing a particulate matter sensor according to an eighth embodiment of the present invention. In this embodiment, the electrode nucleus 3 and the electrode 4 are respectively stacked on or applied to the top surface and the bottom surface of the base 2 that is formed in the shape of a thin sheet, and the heater 8 is formed on the side surface of the base 2. The base 2 may be a structure that is cut from a honeycomb structure in which through holes are formed between the top surface and the bottom surface. This configuration also achieves the desired effects.

Figure 11:
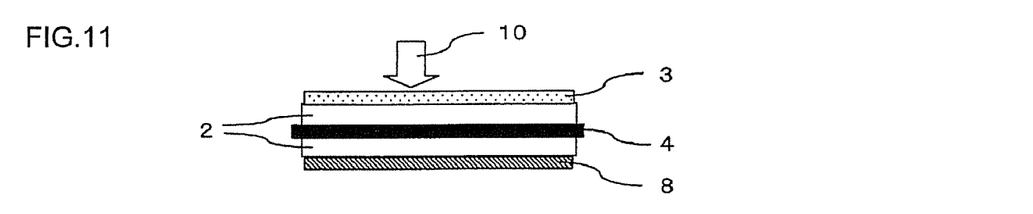
FIG. 11 is a schematic side view showing a particulate matter sensor according to a ninth embodiment of the present invention.

FIG. 11 is a schematic side view showing a particulate matter sensor according to a ninth embodiment of the present invention. In this embodiment, the electrode nucleus 3 and the heater 8 are respectively stacked on or applied to the top surface and the bottom surface of the base 2 that is formed in the shape of a thin sheet, and the electrode 4 is formed on the side surface of the base 2. The base 2 may be a structure that is cut from a honeycomb structure in which through holes are formed between the top surface and the bottom surface. This configuration also achieves the desired effects.

Figure 12:
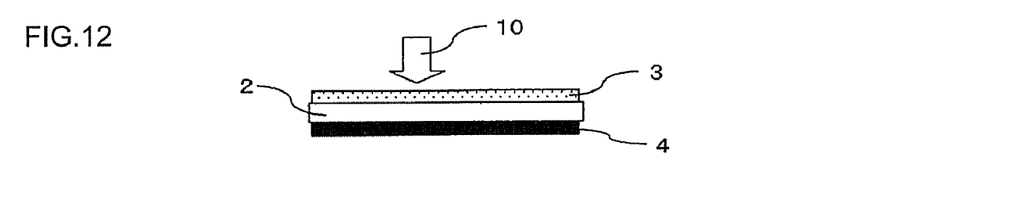
FIG. 12 is a schematic side view showing a particulate matter sensor according to a tenth embodiment of the present invention.

FIG. 12 is a schematic side view showing a particulate matter sensor according to a tenth embodiment of the present invention. In this embodiment, the electrode nucleus 3 and the electrode 4 that also serves as a heater are respectively stacked on or applied to the top surface and the bottom surface of the base 2 that is formed in the shape of a thin sheet. The electrode 4 that also serves as a heater is formed using a member that generates heat when a current flows therethrough. The base 2 may be a structure that is cut from a honeycomb structure in which through holes are formed between the top surface and the bottom surface. This configuration also achieves the desired effects.

[Base]

The base used in the present invention has insulating properties. The material for the base is not particularly limited, but preferably contains a ceramic (i.e., silicon carbide, cordierite, alumina titanate, sialon, mullite, silicon nitride, zirconium phosphate, zirconia, titania, alumina, silica, or a combination of these), or a sintered metal as the main component. Note that a base formed of silicon carbide may exhibit conductivity. Zirconium phosphate and zirconia exhibit oxygen ion conductivity at a high temperature, so that an ion current flows therethrough. Therefore, it is not desirable to use them when the particulate matter sensor is used at a high temperature.

In the present invention, the base has at least a pair of opposing plane surfaces. The shape of the base is not particularly limited. It is preferable to use a ribbon-shaped base. The distance between the pair of opposing plane surfaces of the base may be appropriately selected taking account of thermal impact resistance and mechanical impact resistance (e.g., vibration resistance), but is preferably 0.1 to 10 mm from the viewpoint of requirements (e.g., shape) for onboard applications and impedance change detection sensitivity.

In the present invention, the plane surface of the base on which the electrode nucleus is formed has a centerline average roughness of 0.2 to 200 μm. If the roughness of plane surface is less than 0.2 μm, particulate matter contained in gas flow may not sufficiently adhere to the surface of the base.

The base may be formed so that the electrode nucleus and the electrode are electrically connected when a conductive substance adheres to the base. Specifically, at least one side surface of the base adjacent to the pair of opposing plane surfaces respectively may form an obtuse angle with the surface on which the electrode nucleus is formed and form an acute angle with the surface on which the electrode is formed, so that the electrode nucleus and the electrode are electrically connected when a conductive substance adheres to the side surface and the surface on which the electrode nucleus is formed. The term "at least one side surface" may refer to the side surface that defines the external shape of the base, or the inner surface of a through hole when the base has the through hole. The electrode nucleus and the electrode may be electrically connected by forming the electrode to extend to at least one side surface, or forming the electrode on the side surface.

[Electrode Nucleus]

The term "electrode nucleus" used herein refers to a member that functions as an electrode when a conductive substance adheres to the base. Ideally, the electrode nucleus does not have a conductive area and does not function as an electrode when a conductive substance does not adhere to the base. This case is preferred, because adhesion of only a small amount of conductive particulate matter to the base can be detected. However, the electrode nucleus may be a member having a conductive area in practical applications. It is preferable that the electrode nucleus have an area corresponding to 50% or less of the area of the electrode parallel to the electrode nucleus.

Figure 13:
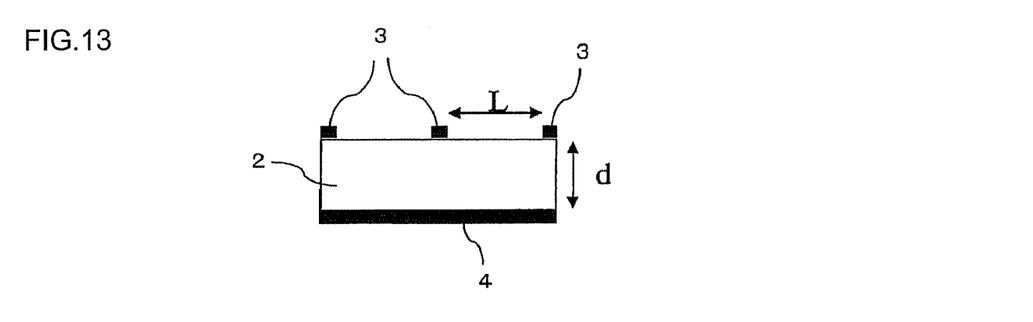
FIG. 13 is a view showing the relationship between an electrode nucleus-electrode nucleus distance L and an electrode nucleus-electrode distance d.

FIG. 13 is a view showing the relationship between an electrode nucleus-electrode nucleus distance L and an electrode nucleus-electrode distance d. In order to efficiently detect a conductive substance that adheres to the entirety of one of the pair of opposing plane surfaces, it is preferable that the electrode nucleus be provided over the entire plane surface. However, the electrode nucleus has a conductive area in practical applications and functions as an electrode even if a conductive substance does not adhere to the base, and an electric field when applying an alternating current between the electrodes is spatial. Therefore, if the adjacent electrode nuclei are positioned too closely with each other, the electrode nuclei function as an integral electrode, so that adhesion of a conductive substance to the plane surface cannot be effectively detected. Therefore, it is preferable to set the electrode nucleus-electrode nucleus distance L on the plane surface so that the electrode nucleus-electrode nucleus distance L and the electrode nucleus-electrode distance d satisfy the relationship "L>d".

The material for the electrode nucleus is not particularly limited, but is preferably a sintered body of a conductive paste, a conductive ceramic, or a metal.

In the present invention, method of forming the electrode nucleus is not particularly limited. If the electrode nucleus is formed by applying a conductive paste (e.g., silver paste) to the base and heating the conductive paste applied to the base, the electrode nucleus can be easily formed while the electrode nucleus is strongly bonded to the base. It is preferable to select the materials for the base and the electrode nucleus so that the difference in coefficient of thermal expansion between the base and the electrode nucleus is $20 \times 10^{-6}/°$ C. or less. For example, when the particulate matter sensor according to the present invention is installed directly under an engine, the particulate matter sensor is subjected to a high temperature during use. In this case, if the difference in coefficient of thermal expansion between the base and the electrode nucleus is too large, the base may break, or the electrode nucleus may be removed from the base. However, such a problem rarely occurs if the difference in coefficient of thermal expansion between the base and the electrode nucleus is $20 \times 10^{-6}/°$ C. or less.

[Electrode]

In the present invention, it is preferable that the electrode be formed on the plane surface of the base on which the electrode nucleus is not formed, or formed inside the base, or formed on the side surface of the base.

In the present invention, the material for the electrode is not particularly limited, but is preferably a sintered body of a conductive paste, a conductive ceramic, or a metal.

In the present invention, a method of forming the electrode is not particularly limited. If the electrode is formed by applying a conductive paste (e.g., silver paste) to the base and heating the conductive paste applied to the base, the electrode can be easily formed while the electrode is strongly bonded to the base.

It is preferable to select the materials for the base and the electrode so that the difference in coefficient of thermal expansion between the base and the electrode is $20 \times 10^{-6}/°$ C. or less. For example, when the particulate matter sensor according to the present invention is installed directly under an engine, the particulate matter sensor is subjected to a high temperature during use. In this case, if the difference in coefficient of thermal expansion between the base and the electrode is too large, the base may break, or the electrode may be removed from the base. However, such a problem rarely occurs if the difference in coefficient of thermal expansion between the base and the electrode is $20 \times 10^{-6}/°$ C. or less.

[Particulate Matter Measurement]

In the present invention, the amount of particulate matter that adheres to the base is determined by utilizing the electrode nucleus and the electrode provided on the base. Specifically, since particulate matter contained in exhaust gas is conductive and the impedance between the electrodes is inversely proportional to the electrode area, the amount of particulate matter that adheres to the base is determined by measuring the impedance between the electrodes by utilizing the particulate matter that adheres to one plane surface of the base as an electrode. Specifically, the particulate matter sensor according to the present invention can measure a change in conductive parts area on one plane surface of the base due to particulate matter that adheres to the plane surface by measuring the alternating-current impedance between the electrode nucleus and the electrode provided on the base. Since the conductive parts area on the plane surface changes corresponding to the absolute amount of conductive particulate matter that adheres to the base, the amount of particulate matter that adheres to the base can be uniquely determined from the measurement data that indicates electrical properties (e.g., alternating-current impedance). More specifically, the relationship between the mass of the particulate matter that adheres to the base and the electrical properties (e.g., alternating-current impedance) is graphed in advance based on the measured values, for example. The amount of particulate matter that adheres to the base when measuring the electrical properties (e.g., alternating-current impedance) is determined based on the above relationship.

In the present invention, the amount of particulate matter that adheres to the base can thus be determined based on the measured alternating-current impedance. However, it is preferable to provide a coil (inductance) in an impedance measurement circuit in order to determine the amount of particulate matter that adheres to the base with higher accuracy. If the coil is thus provided in the impedance measurement circuit, the alternating-current impedance of a circuit that includes the coil and a capacitive filter rapidly approaches zero under a resonance condition "$L\omega=1/C\omega$" (where, L: inductance, C: capacitance, $\Omega$: $2\pi f$ (f: frequency)). Therefore, a change in alternating-current impedance occurs steeply due to a change in the amount of particulate matter that adheres to the base, so that the amount of particulate matter that adheres to the base can be determined with higher accuracy.

The inductance of the coil provided in the impedance measurement circuit may be set so that the resonance condition is satisfied when the amount of particulate matter that adheres to the base has reached a target value. Specifically, the inductance of the coil is controlled in advance utilizing a variable inductance or the like so that the alternating-current impedance rapidly approaches zero when the amount of particulate matter that adheres to the base has reached a given value. Note that the resonance condition may also be adjusted by providing a capacitance, a DC resistance, or the like other than inductance in series or parallel in the impedance measurement circuit, in the present invention.

The frequency of the alternating current when measuring the alternating-current impedance of the honeycomb structure according to the present invention is preferably 100 Hz to 10 MHz. If the frequency is less than 100 Hz, the impedance of the honeycomb structure increases to a large extent, so that it is necessary to handle a very small current during the impedance measurement. Therefore, the particulate matter measurement accuracy may decrease due to noise. If the frequency is more than 10 MHz, the effect of the inductance of the entire measurement system including a signal lead line from the honeycomb structure and the like can not be ignored and may induce resonance with a parasitic capacitance of the honeycomb structure or the line. This may make it difficult to detect the signal, so that the measurement accuracy may decrease. The frequency of the alternating current when measuring the alternating-current impedance is preferably 1 to 100 kHz, since the sensitivity increases as the frequency decreases.

EXAMPLES

The present invention is further described below by way of examples. Note that the present invention is not limited to the following examples.

Example 15 to 25 mass % of graphite and 5 to 15 mass % of a synthetic resin (e.g., PET, PMA, or phenol resin) as pore-forming agents were added to a cordierite-forming raw material prepared by mixing a talc powder, a kaolin powder, a calcined kaolin powder, an alumina powder, an aluminum hydroxide powder, and a silica powder so that the $SiO_2$ content was 42 to 56 mass %, the $Al_2O_3$ content was 0 to 45 mass %, and the MgO content was 12 to 16 mass %. After the addition of predetermined amounts of methyl cellulose and a surfactant, water was added to the mixture. The mixture was then kneaded to obtain a clay. The clay was degassed under vacuum, and extruded into a honeycomb structure. The honeycomb structure was subjected to microwave drying and hot air drying, and fired at a maximum temperature of 1400 to 1435° C. to obtain a honeycomb structure formed of a porous ceramic (cordierite) (thickness: 3 mm, cell wall thickness: 0.3 mm, cell density: 300 cpsi). The honeycomb structure was cut to have a width of 6 mm, a length of 50 mm, and a thickness of 3 mm, and plugged in a checkered pattern as shown in FIG. 4. A silver paste was applied to one plane surface of the honeycomb structure in a pattern shown in FIG. 4 (i.e., the silver paste was applied linearly along the longitudinal direction at the center of the plane surface in the latitudinal direction, and was also applied on the plugs). The silver paste was also applied to the entirety of the other plane surface (see FIG. 3). The honeycomb structure was then fired to form an electrode nucleus and an electrode. An impedance measurement circuit for measuring the alternating-current impedance between the electrodes was connected to the honeycomb structure. The resulting particulate matter sensor was disposed in an exhaust gas passage.

Figure 14:
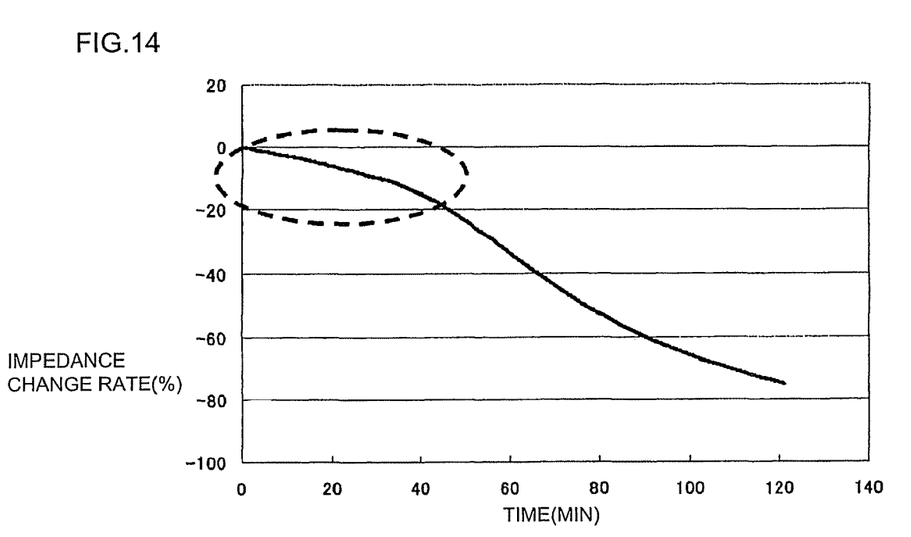
FIG. 14 is a graph showing the relationship between the impedance change rate and time during usage of a particulate matter sensor according to the example.

A diesel engine exhaust gas was caused to flow through the exhaust gas passage, and the alternating-current impedance between the electrode nucleus and the electrode was measured while allowing particulate matter to adhere to the particulate matter sensor. FIG. 14 shows the relationship between the elapsed time and the change rate of the measured alternating-current impedance. A diesel engine (displacement: 2 l) was operated at an engine speed and a torque of 1950 rpm and 40 Nm. An EGR valve was opened by 41%. The exhaust gas temperature was 225° C., the exhaust gas flow rate was 1.3 $Nm^3$/min, and the particulate matter concentration was 6.8 $mg/m^3$. As shown in FIG. 14, the amount of particulate matter adhering to the particulate matter sensor had a correlation with a change in impedance.

According to the embodiments of the present invention in which the particulate matter sensor includes the heater, the particulate matter concentration can be measured with high accuracy using only the area enclosed by a dotted line in FIG. 14 by burning out the particulate matter that adheres to the particulate matter sensor using the heater.

INDUSTRIAL APPLICABILITY

The present invention may be used for a particulate filter (e.g., DPF) and an onboard particulate diagnostic sensor.

The invention claimed is:

1. A particulate matter sensor comprising:
   an insulating base that has at least a pair of opposing plane surfaces;
   an electrode nucleus that is formed only on one of the pair of opposing plane surfaces of the base, said electrode nucleus forming an electrode when a conductive substance adheres to the plane surface; and
   another electrode that is disposed parallel to said electrode nucleus and is provided on the other of the pair of opposing plane surfaces, or provided on a side surface of the base that is adjacent to the pair of opposing plane surfaces, or provided inside the base,
   wherein said electrode nucleus has an area corresponding to 50% or less of the area of the electrode parallel to said electrode nucleus.

2. The particulate matter sensor according to claim 1, wherein the base has a plurality of through-holes that are formed through the pair of opposing plane surfaces.

3. The particulate matter sensor according to claim 2, wherein the plane surface on which said electrode nucleus is formed has a centerline average roughness of 0.2 to 200 μm.

4. The particulate matter sensor according to claim 2, further comprising an isolated electrode nucleus that is electrically isolated from said electrode nucleus.

5. The particulate matter sensor according to claim 4, further comprising a heater that is provided inside the base, or provided on the side surface of the base that is adjacent to the pair of opposing plane surfaces, or provided on the plane surface on which said electrode nucleus is not formed.

6. The particulate matter sensor according to claim 1, wherein the plane surface on which said electrode nucleus is formed has a centerline average roughness of 0.2 to 200 μm.

7. The particulate matter sensor according to claim 1, further comprising an isolated electrode nucleus that is electrically isolated from said electrode nucleus.

8. The particulate matter sensor according to claim 7, further comprising a heater that is provided inside the base, or provided on the side surface of the base that is adjacent to the pair of opposing plane surfaces, or provided on the plane surface on which said electrode nucleus is not formed.

9. The particulate matter sensor according to claim 8, wherein said electrode nucleus and the electrode are electrically connected when a conductive substance adheres to the base.

10. The particulate matter sensor according to claim 7, wherein said electrode nucleus and the electrode are electrically connected when a conductive substance adheres to the base.

11. A particulate matter measuring method comprising:

disposing an electrode nucleus only on at least one of a pair of opposing plane surfaces of an insulating base, and disposing another electrode that is parallel to said electrode nucleus, said electrode nucleus forming an electrode when a conductive substance adheres to the plane surface, and the electrode being provided on the other of the pair of opposing plane surfaces, or provided on a side surface of the base that is adjacent to the pair of opposing plane surfaces, or provided inside the base, wherein said electrode nucleus has an area corresponding to 50% or less of the area of the electrode parallel to said electrode nucleus;

disposing the base in a gas passage so that the plane surface on which said electrode nucleus is formed is positioned on an upstream side in the gas passage;

measuring the impedance between said electrode nucleus and the electrode while causing an alternating current to flow between said electrode nucleus and the electrode; and determining the amount of conductive particulate matter that adheres to the base based on the impedance that has been measured.

* * * * *